United States Patent
Kaifu et al.

(10) Patent No.: US 6,847,698 B2
(45) Date of Patent: Jan. 25, 2005

(54) RADIATION IMAGE SENSING APPARATUS

(75) Inventors: Noriyuki Kaifu, Tokyo (JP); Kazuaki Tashiro, Kanagawa (JP); Osamu Yuki, Tokyo (JP)

(73) Assignee: Canon Kabushiki Kaisha, Tokyo (JP)

( * ) Notice: Subject to any disclaimer, the term of this patent is extended or adjusted under 35 U.S.C. 154(b) by 7 days.

(21) Appl. No.: 09/916,269

(22) Filed: Jul. 30, 2001

(65) Prior Publication Data

US 2002/0025022 A1 Feb. 28, 2002

(30) Foreign Application Priority Data

Aug. 1, 2000 (JP) ....................................... 2000-233651

(51) Int. Cl.⁷ ............................................... H05G 1/14
(52) U.S. Cl. ..................... 378/97; 378/98.8; 378/96; 378/98.7; 378/108; 378/114; 250/370.09; 250/370.07
(58) Field of Search .......................... 349/97, 98.8, 96, 349/98.7, 108, 114, 370.09, 370.07; 378/97, 98.8, 96, 98.7, 108, 114; 250/370.09, 370.07

(56) References Cited

U.S. PATENT DOCUMENTS

| | | | | |
|---|---|---|---|---|
| 4,803,550 A | * | 2/1989 | Yabe et al. | .................... 348/68 |
| 5,528,043 A | * | 6/1996 | Spivey et al. | ............. 250/208.1 |
| 5,778,044 A | * | 7/1998 | Bruijns | .................... 378/98.12 |

FOREIGN PATENT DOCUMENTS

| EP | 0 881 828 | 12/1998 |
|---|---|---|
| JP | 7-171142 | 7/1995 |
| JP | 10-327317 | 12/1998 |

* cited by examiner

Primary Examiner—Tarifur R. Chowdhury
Assistant Examiner—George Y. Wang
(74) Attorney, Agent, or Firm—Fitzpatrick, Cella, Harper & Scinto (57) ABSTRACT

When a phototimer unit is used for exposure control, a deterioration in a S/N ratio occurs, and optimal exposure cannot be performed due to a deviation from a proper image sensing position and the like. Therefore, there is provided a radiation image sensing apparatus comprising an X-ray image sensing panel which is capable of non-destructive reading and adapted to sense an object image by allowing radiation from an X-ray source to pass through an object, and a control circuit adapted to perform control to stop emission of radiation from the X-ray source on the basis of a signal obtained from the X-ray image sensing panel by non-destructive reading in the image sensing operation.

21 Claims, 11 Drawing Sheets

RADIATION IMAGE SENSING APPARATUS

BACKGROUND OF THE INVENTION

1. Field of the Invention

The present invention relates to a radiation image sensing apparatus using X-rays or the like, which is used for radiologic equipment or the like and an image sensing method for the radiation image sensing apparatus and, more particularly, to a controller for performing emission stop control on radiation such as X-rays.

2. Related Background Art

Figure 9:
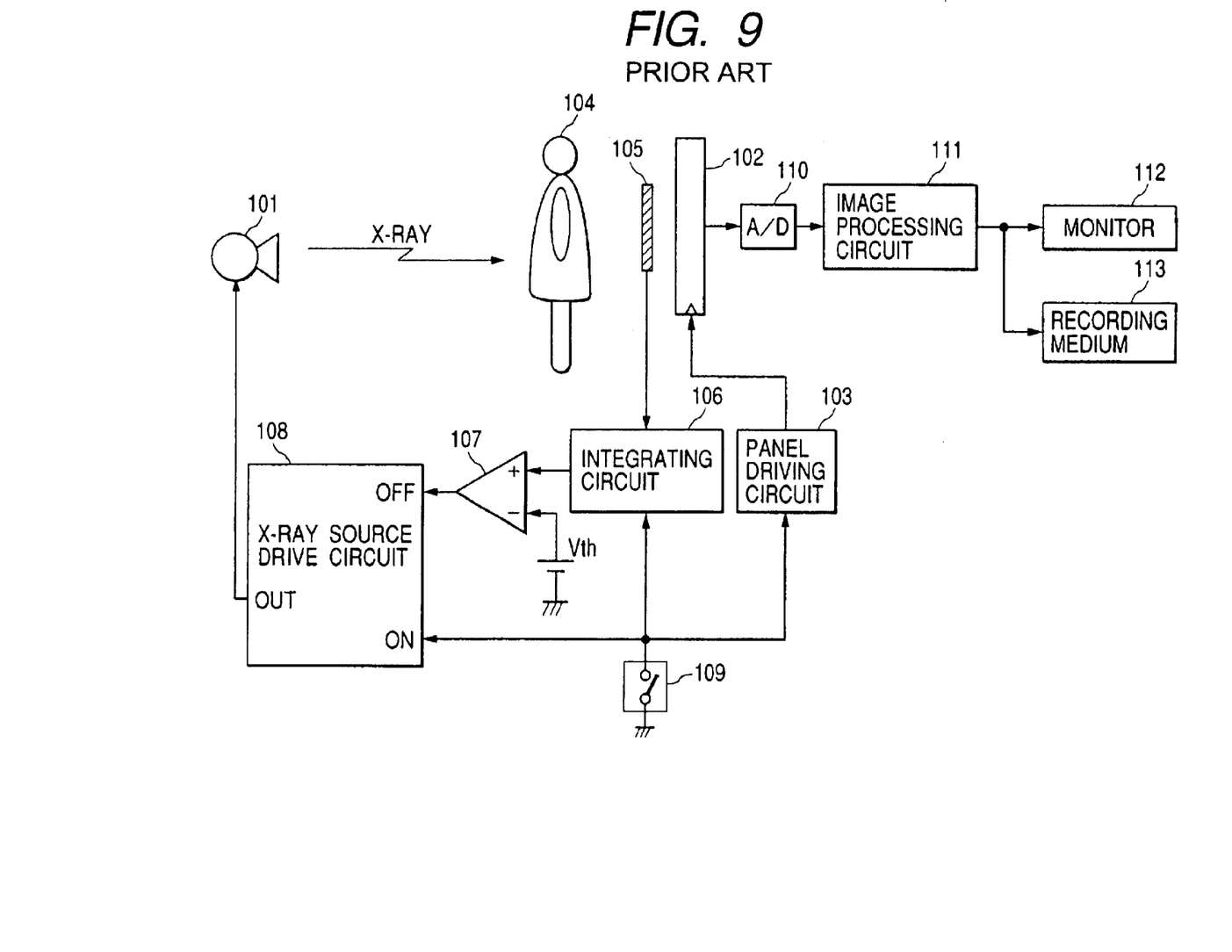
FIG. 9 is a block diagram showing a conventional X-ray image sensing apparatus.

As an X-ray image sensing apparatus, the present applicant has proposed an image sensing apparatus and method which perform exposure control by using a phototimer in, for example, Japanese Laid-Open Patent Application No. 10-327317. FIG. 9 is a block diagram showing the image sensing apparatus disclosed in this reference. Referring to FIG. 9, this apparatus includes an X-ray source 101 for emitting X-rays in the form of pulses and an X-ray image sensing panel 102. The X-ray image sensing panel 102 is comprised of a plurality of photoelectric conversion elements arranged two-dimensionally and a drive circuit of the elements. The X-ray image sensing panel 102 is driven by a panel drive circuit 103.

A phototimer unit 105 is arranged between the X-ray image sensing panel 102 and an object 104. The phototimer unit 105 is a sensor for detecting X-rays transmitted through a reference part (e.g., alveolar part) of the object 104 during image sensing exposure. Outputs from the phototimer unit 105 are integrated by an integrating circuit 106. The resultant value is output to a comparator 107. The comparator 107 compares this integration output with a reference value $V_{th}$, and outputs the comparison result to an X-ray source drive circuit 108 for driving the X-ray source 101. The X-ray source drive circuit 108 is controlled by an output signal from the comparator 107. When the output from the integrating circuit 106 exceeds the reference value $V_{th}$, the X-ray source drive circuit 108 stops driving the X-ray source 101 to stop X-ray emission.

This apparatus also includes a sensing start switch 109 for designating the start of image sensing of the object 104, an A/D converter 110 for A/D-converting a signal from the X-ray image sensing panel 102, an image processing circuit 111 for processing an image signal from the A/D converter 110, a monitor 112 for displaying a sensed image, and a recording medium 113 for recording sensed image data.

Figure 10:
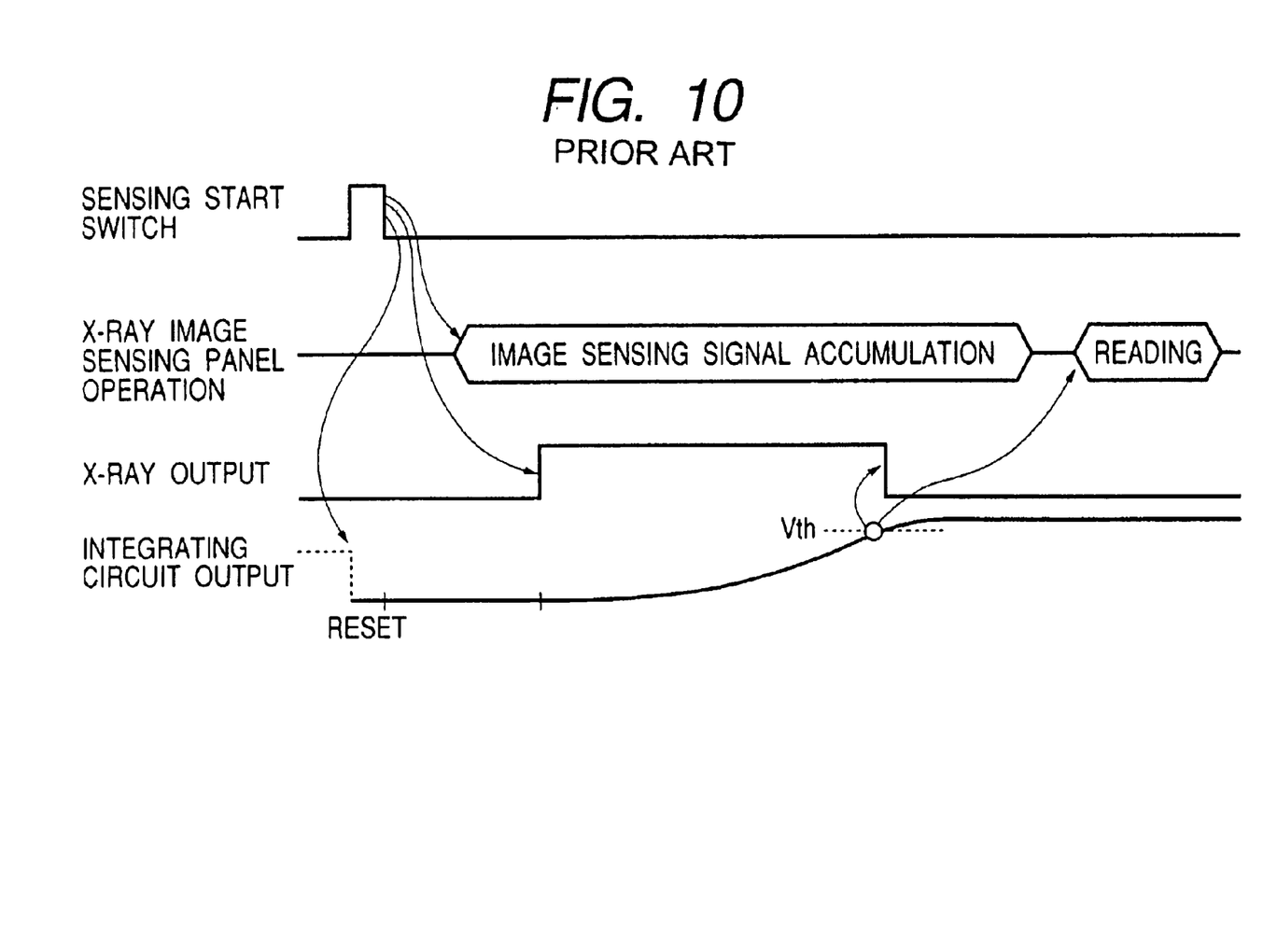
FIG. 10 is a timing chart for explaining the operation of the conventional apparatus in FIG. 9.

FIG. 10 is a timing chart showing the operation of the image sensing apparatus in FIG. 9. When the sensing start switch 109 is turned on, a signal for designating the start of image sensing operation is supplied from the sensing start switch 109 to the panel drive circuit 103, integrating circuit 106, and X-ray source drive circuit 108 (the sensing start switch in FIG. 10). Upon reception of this signal from the sensing start switch 109, the X-ray source drive circuit 108 starts driving the X-ray source 101 to emit X-rays from the X-ray source 101 (X-ray output in FIG. 10). Upon reception of the signal from the sensing start switch 109, the panel drive circuit 103 starts driving the X-ray image sensing panel 102 (X-ray image sensing panel operation in FIG. 10). The integrating circuit 106 resets an output from the phototimer unit 105 and starts integration (integrating circuit output in FIG. 10).

The X-rays emitted from the X-ray source 101 are transmitted through the object 104 which is a patient to be diagnosed. At this time, the X-rays transmitted through the object 104 vary in transmission amount depending on the sizes and shapes of bones and internal organs, the presence/absence of a focus, and the like in the object 104, and include image information about them. The X-rays transmitted through the phototimer unit 105 are converted into visible light by a phosphor (not shown). This light is incident on the X-ray image sensing panel 102. In the X-ray image sensing panel 102, sensed signals are accumulated by the photoelectric conversion elements arranged two-dimensionally (X-ray image sensing panel operation in FIG. 10).

The integrating circuit 106 integrates outputs from the phototimer unit 105. The output from the integrating circuit 106 gradually increases (integrating circuit output in FIG. 10). When the output from the integrating circuit 106 exceeds the reference value $V_{th}$, the comparator 107 outputs a signal for designating a driving stop to the X-ray source drive circuit 108, thereby stopping X-ray emission from the X-ray source 101 (X-ray output in FIG. 10). Thereafter, the image processing circuit 111 reads the sensed signal through the A/D converter 110 and performs predetermined image processing. The image processing circuit 111 also displays the sensed image on the monitor 112 or records the image data on the recording medium 113 (X-ray image sensing panel operation in FIG. 10).

In the above conventional X-ray image sensing apparatus, however, since interruption of X-rays is controlled by using the phototimer unit, the following problems arise. The phototimer is very expensive, and X-rays are slightly attenuated when they pass through the phototimer unit, resulting in a deterioration in S/N characteristics.

Figure 11:
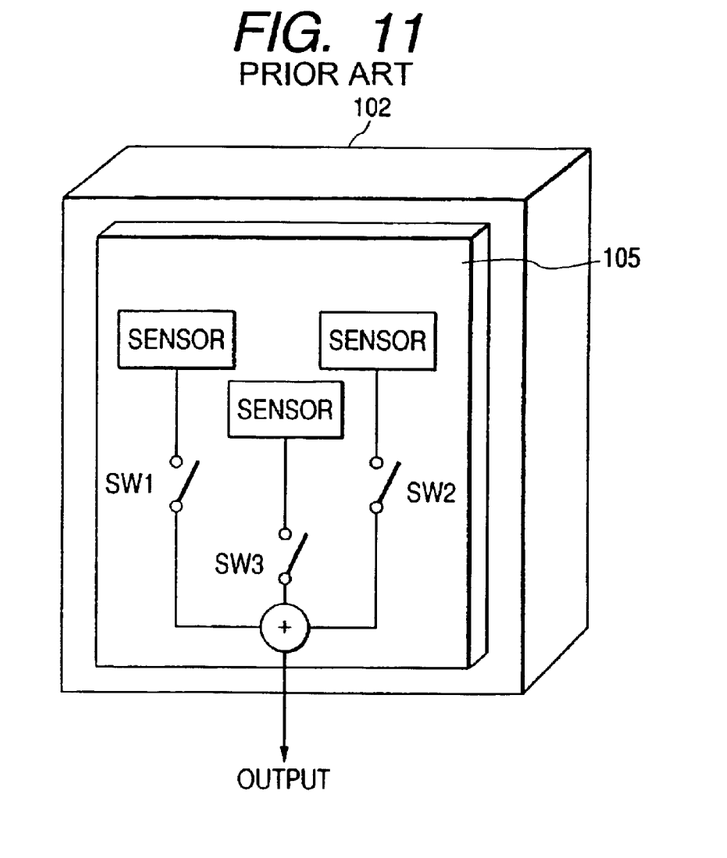
FIG. 11 is a view showing the phototimer unit in FIG. 9.
Figure 12A:
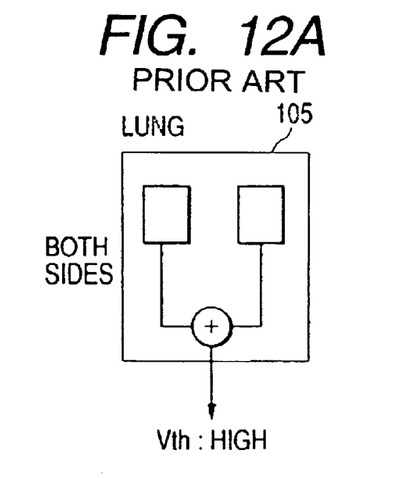
FIGS. 12A and 12B are views for explaining how a sensor is selected in accordance with an image sensing position.
Figure 12B:
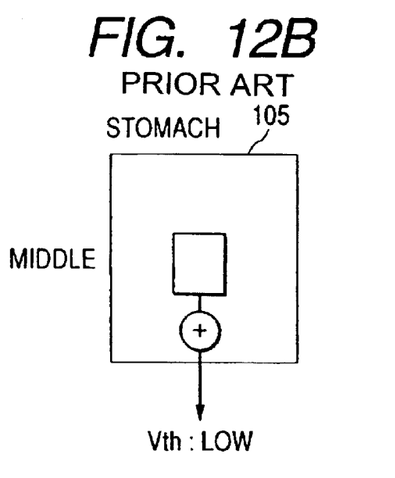

When the phototimer unit is used, a doctor or examination technician selects one or two of switches SW1 to SW3 in accordance with an image sensing position before image sensing to select a sensor for detecting X-rays, as shown in FIG. 11. When, for example, the lung of the object 104 is to be sensed, the two side sensors are selected, as shown in FIG. 12A. When the stomach is to be sensed, the central sensor is selected, as shown in FIG. 12B. In addition, the doctor or examination technician determines the reference value $V_{th}$ for the integrating circuit 106 in accordance with an image sensing position before image sensing. When, for example, the lung of a person is to be sensed, since a high S/N ratio is required, the reference value $V_{th}$ is set to be high. When the stomach is to be sensed, since high contrast can be obtained owing to barium, the reference value $V_{th}$ is set to be low.

Selecting sensors and setting a reference value in accordance with an image sensing position lead to a deterioration in operability. In addition, if the image sensing position deviates from a proper position, the error between the X-ray amount at the actual image sensing position and the amount detected by the sensor increases. Optimal exposure cannot therefore be performed, resulting in a decrease in S/N ratio, an increase in X-ray dose, and a deterioration in image quality.

SUMMARY OF THE INVENTION

It is an object of the present invention to provide a radiation image sensing apparatus which can easily and accurately perform optimal exposure and obtain a high-quality image without any deterioration in S/N characteristics, and an image sensing method for the radiation image sensing apparatus.

In order to achieve the above object, according to aspect of the present invention, there is provided a radiation image sensing apparatus comprising an image sensing unit which is capable of non-destructive reading, adapted to sense an object image by allowing radiation from a radiation source to pass through an object, and a control unit adapted to perform control to stop emission of radiation from the radiation source on the basis of a signal obtained from the image sensing unit by non-destructive reading in the image sensing operation.

In addition, according to another aspect of the present invention, there is provided an image sensing method for a radiation image sensing apparatus including an image sensing unit which is capable of non-destructive reading and adapted to sense an object image by allowing radiation from a radiation source to pass through an object, comprising a step of performing control to stop emission of radiation from the radiation source on the basis of a signal obtained from the image sensing unit by non-destructive reading in the image sensing operation.

The other objects and features of the present invention will be apparent from the following detailed description in conjunction with the accompanying drawings.

DETAILED DESCRIPTION OF THE PREFERRED EMBODIMENTS

Figure 1:
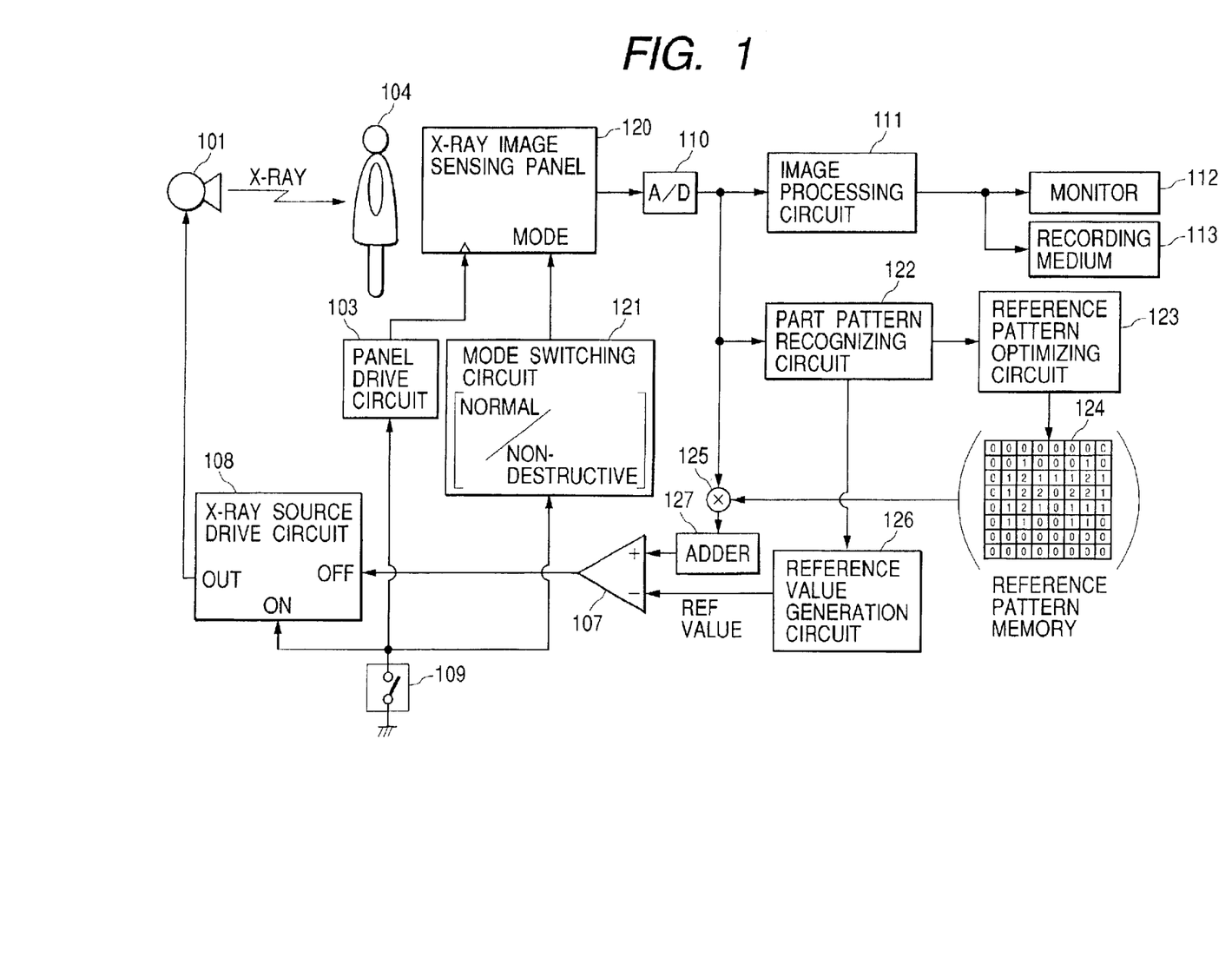
FIG. 1 is a block diagram showing the arrangement of a radiation image sensing apparatus according to the first embodiment of the present invention.

The embodiments of the present invention will be described in detail below with reference to the accompanying drawings. FIG. 1 is a block diagram showing the arrangement of a radiation image sensing apparatus according to the first embodiment of the present invention. The same reference numerals as in FIG. 1 denote the same parts in FIG. 9, and a description thereof will be omitted. In this embodiment, for example, still images of the human lung, stomach, and the like are sensed, and X-ray emission stop control is performed by using a non-destructive reading output in place of a conventional phototimer unit. Referring to FIG. 1, an X-ray image sensing panel 120 is an image sensing panel capable of normal reading and non-destructive reading. The X-ray image sensing panel 120 is comprised of a plurality of photoelectric conversion elements arranged two-dimensionally and a drive circuit of the elements. The circuit arrangement and operation of the X-ray image sensing panel 120 will be described in detail later.

A mode switching circuit 121 is a circuit for switching the reading mode of the X-ray image sensing panel 120 to the normal reading mode or the non-destructive reading mode. A part pattern recognizing circuit 122 is a circuit for performing pattern recognition of the image sensed by the X-ray image sensing panel 120 on the basis of an output value from an A/D converter 110. More specifically, the part pattern recognizing circuit 122 performs pattern recognition on the basis of the output values of all pixels from the A/D converter 110 to identify the sensed image (e.g., the lung, stomach, hand, or the like). As a consequence, the position and size of the sensed image are known.

A reference pattern optimizing circuit 123 is a circuit for determining an optimal value for each pixel of a reference pattern on the basis of the recognition result obtained by the part pattern recognizing circuit 122. More specifically, the reference pattern optimizing circuit 123 determines on the basis of the pattern recognition result which position of the image subjected to pattern recognition is to be mainly seen, and then stores the numerical value determined for each pixel into a reference pattern memory 124. In this embodiment, for the sake of descriptive convenience, as shown in FIG. 1, weighting is performed in three levels, namely 0, 1, and 2. In this case, "0" indicates a position other than a position to be examined (a position that need not be examined); "2", a position that should be mainly examined; and "1", a value that makes an image better as a whole. In this embodiment, for the sake of descriptive convenience, weighting is performed in three levels. Obviously, however, an image with higher quality can be obtained by performing weighting in more levels.

A reference value generation circuit 126 is a circuit for generating a reference value (REF value) on the basis of the pattern recognition result obtained by the part pattern recognizing circuit 122. More specifically, in the reference value generation circuit 126, REF values are determined in advance in accordance with images. For example, if a pattern recognition result indicates the lung, a large REF value is set because the lung demands a high S/N ratio. If the pattern recognition result indicates the stomach, a small REF value is set.

Referring to FIG. 1, for the sake of illustrative convenience, the reference pattern memory 124 has a storage area corresponding to 8×8 pixels, and stores numerical values each weighted with one of 0 to 2 for each pixel. In practice, however, the X-ray image sensing panel 120 has much more pixels, and the reference pattern memory 124 has a larger storage area accordingly.

A multiplier 125 is a circuit for multiplying the numerical value of each pixel in the reference pattern memory 124 by the A/D conversion output value for each pixel of the X-ray image sensing panel 120. The multiplier 125 multiplies the values of corresponding pixels and outputs the calculation result to an adder 127. An output value from the adder 127 is the result of weighted addition of an A/D conversion output value and a corresponding value in the reference pattern memory 124. A comparator 107 compares an output value from the adder 127 with the REF value from the reference value generation circuit 126. If the output value from the adder 127 becomes equal to or larger than the REF value, the comparator 107 outputs to an X-ray drive circuit 108 a signal for instructing an X-ray source 101 to stop, thereby stopping X-ray emission.

In this embodiment, as a control circuit for controlling to stop emission of radiation from the radiation source on the basis of the signal obtained from the X-ray image sensing panel by the non-destructive reading operation, the circuit constituted by the part pattern recognizing circuit, reference pattern optimizing circuit, reference pattern memory, multiplier, adder, reference value generation circuit, and comparator has been described. However, this circuit may be replaced with a circuit having only a comparator for comparing a predetermined reference value with a non-destructive reading signal and performing control to stop X-ray emission when a non-destructive reading signal becomes equal to or larger than the predetermined value.

Note that a sensing start switch 109, image processing circuit 111, monitor 112, and recording medium 113 are identical to those shown in FIG. 9. An illustration of a phosphor for converting X-rays into visible light is omitted from FIG. 1 like FIG. 9.

Figure 2:
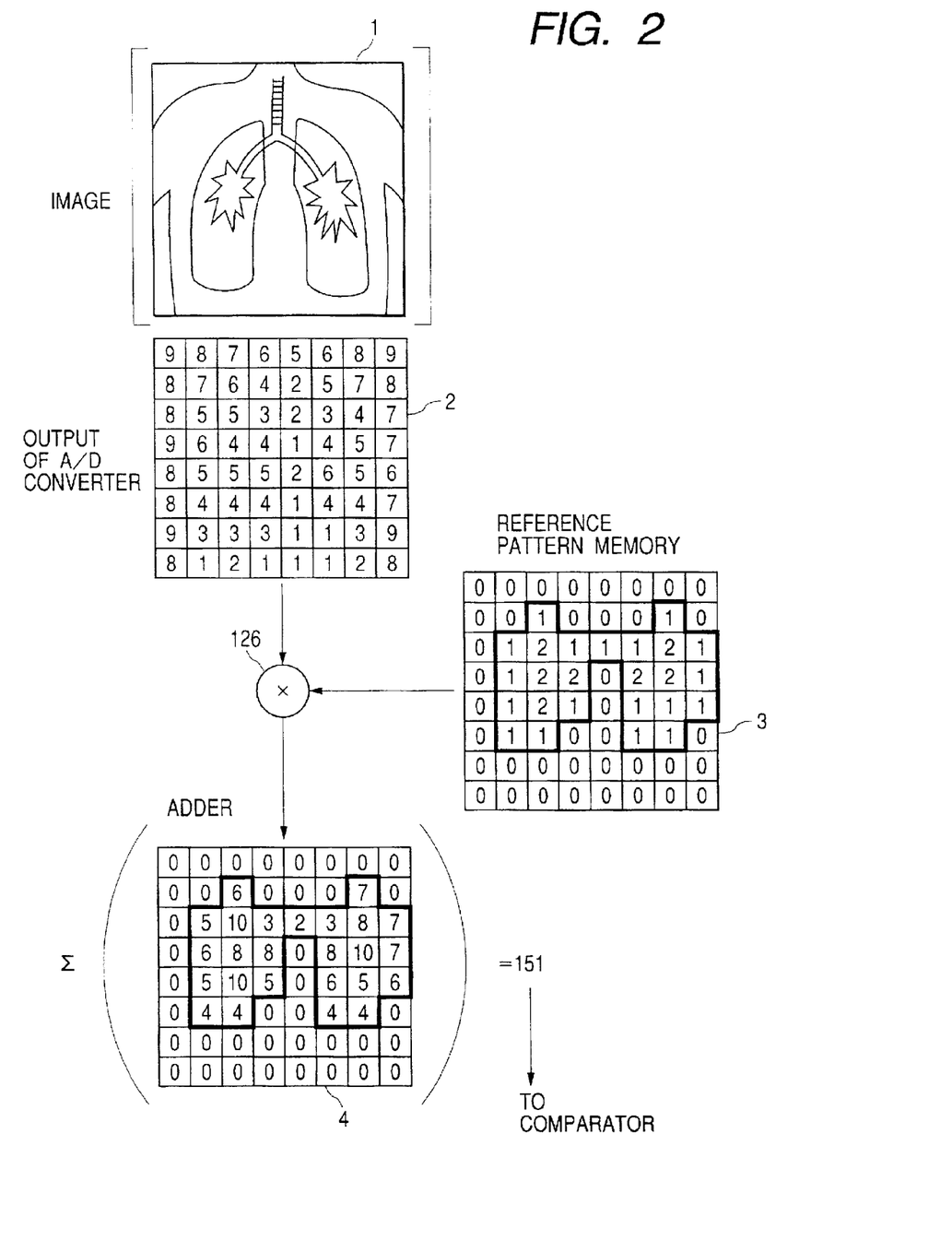
FIG. 2 is a view for explaining how an exposure amount is calculated by weighted addition in the first embodiment.

FIG. 2 is a view for explaining exposure amount detecting operation in this embodiment. FIG. 2 shows an image 1 on the X-ray image sensing panel 120, an output value 2 from the A/D converter 110 for each pixel of the X-ray image sensing panel 120, a numerical value 3 of each pixel in the reference pattern memory 124, and a numerical value 4 for each pixel in the adder 127. For the sake of illustrative convenience, FIG. 2 also shows the X-ray image sensing panel 120 having 8×8 pixels.

As described above, the multiplier 125 multiplies the output value 2 from the A/D converter 110 for each pixel X-ray image sensing panel 120 by the numerical value 3 for each pixel from the reference pattern memory 124. The output from the multiplier 125 is output to the adder 127. The adder 127 adds the numerical values 4 of all pixels. In this case, the output value (151 in FIG. 2) from the adder 127 is output to the comparator 107 as a numerical value representing the current exposure amount. If this addition value exceeds the REF value, the comparator 107 determines that the current exposure amount has reached the optimal exposure amount, and outputs a stop signal to the X-ray drive circuit 108 to stop X-ray emission.

Figure 3:
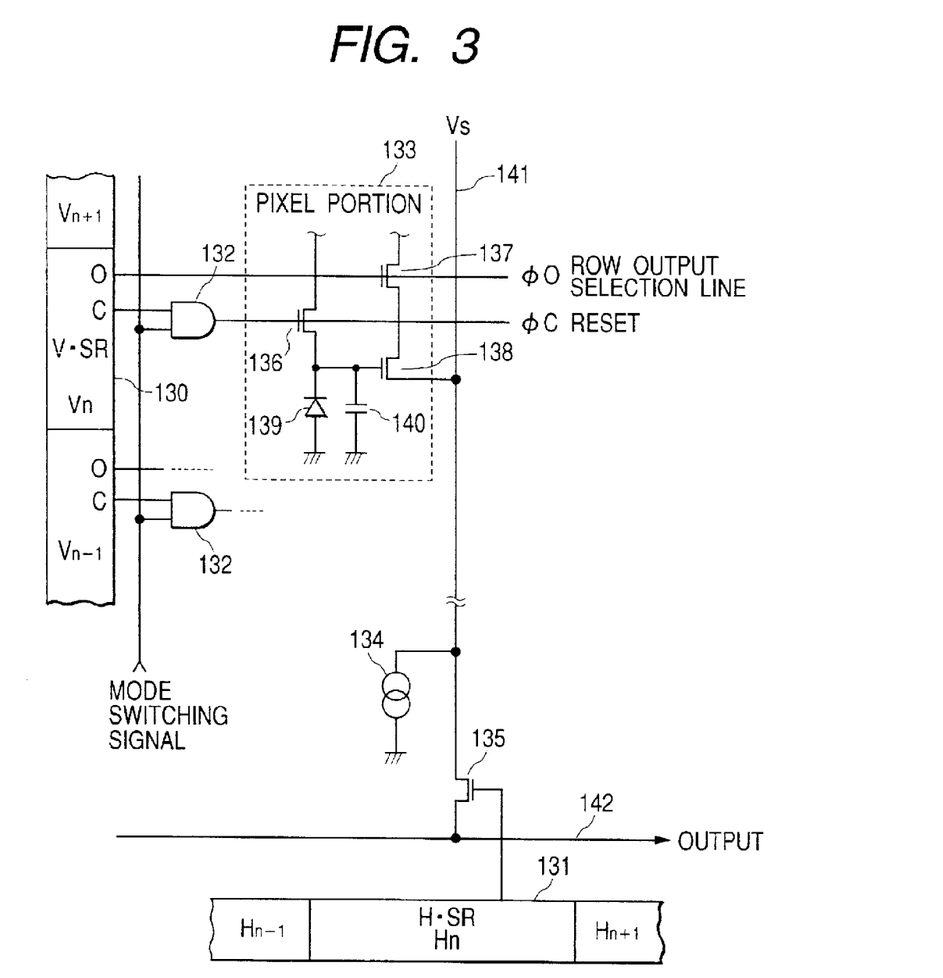
FIG. 3 is a circuit diagram showing part of a circuit for an X-ray image sensing panel in the embodiment shown in FIG. 1.

FIG. 3 is a circuit diagram showing the circuit of the X-ray image sensing panel 120. FIG. 3 shows part of the circuit of the X-ray image sensing panel 120. Referring to FIG. 3, this circuit includes a vertical shift register 130, horizontal shift register 131, AND gate 132, and pixel portion 133. The circuit also includes a constant current source 134 and horizontal switching MOS transistor 135. The AND gate 132 receives a signal for designating a reading mode from the mode switching circuit 121 in FIG. 1, i.e., a mode switching signal for designating the normal reading mode or non-destructive reading mode. In addition, the circuit includes a vertical reading line 141 and horizontal reading line 142.

The pixel portion 133 is comprised of a reset MOS transistor 136, vertical output switching MOS transistor 137, reading MOS transistor 138, photoelectric conversion element 139, and capacitor 140. The pixel portion 133 constitutes an amplifier having a voltage amplification factor of 1, together with the constant current source 134. In reading operation, the charge in the photoelectric conversion element 139 does not move, and reading operation can be performed independently of reset operation.

More specifically, the photoelectric conversion element 139 and capacitor 140 are connected to the gate terminal of the reading MOS transistor 138 of the pixel portion 133 to constitute a source-follower circuit, together with the constant current source 134. With this arrangement, no current flows in the gate terminal of the reading MOS transistor 138, and signal charge information in the photoelectric conversion element 139 can be output to the vertical reading line 141. During reading operation, no signal charge in the photoelectric conversion element 139 moves. This makes it possible to perform non-destructive reading. Although a resistor may be used in place of the constant current source 134, the constant current source 134 is preferably used to improve the precision. In this embodiment, a photoelectric conversion element is connected to the gate terminal of each reading MOS transistor. However, the present invention is not limited to this. Non-destructive reading can also be performed by connecting a photoelectric conversion element to an element having an amplifying function or the control terminal of the circuit. This is because no current flows in the control terminal and no charge moves. Even if a current flows in the control terminal, only a current or charge much smaller than the current or charge required for output operation flows in the control terminal owing to the principle of amplification. Such the small current can be neglected. Even if, for example, a photoelectric conversion element is connected to the base terminal of a reading bipolar transistor, non-destructive reading can be performed.

Figure 4A:
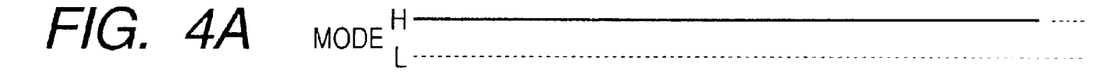
FIGS. 4A, 4B, 4C, 4D, 4E, 4F, 4G, 4H, 4I and 4J are timing charts showing normal reading operation.
Figure 4B:
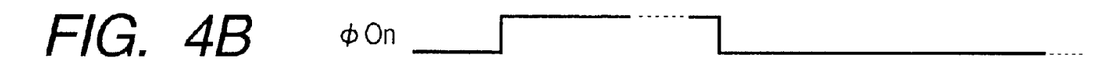

FIGS. 4A to 4J are timing charts showing normal reading operation with reset. FIGS. 5A to 5J are timing charts showing non-destructive reading operation. Normal reading operation will be described first with reference to FIGS. 4A to 4J. In normal reading operation, as shown in FIG. 4A, a high-level mode switching signal is supplied from the mode switching circuit 121 to the AND gate 132 of the X-ray image sensing panel 120. If $\phi O_n$ (high level) is output from the vertical shift register 130 in this state as shown in FIG. 4B, the vertical output switching MOS transistor 137 is turned on.

At this time, since the circuit including the reading MOS transistor 138 constitutes a source follower, which is an amplifying circuit having a voltage amplification factor of about 1, the signal charge in the photoelectric conversion element 139 is directly output to the vertical reading line 141. Although not shown in FIG. 3, a plurality of pixel portions are arrayed in the row direction, and the signal charge in each of the pixel portions corresponding to one line in the row direction is output to the vertical reading line 141. Referring to FIG. 3, a plurality of pixel portions are arrayed in the column direction, and a plurality of pixel portions 133 are arranged in the row and column directions in the form of a matrix.

Figure 4C:
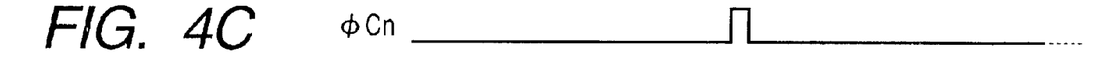
Figure 4D:
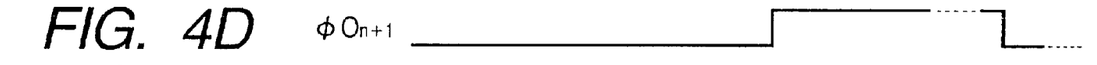
Figure 4E:
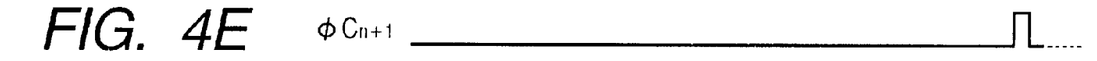
Figure 4F:
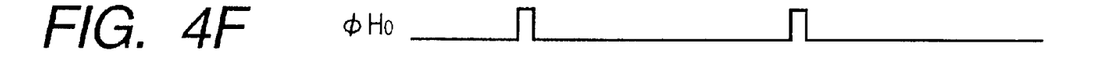
Figure 4G:
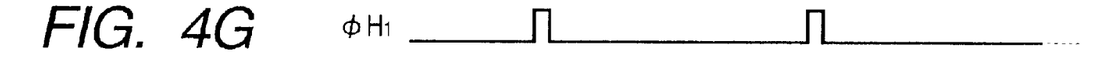
Figure 4H:
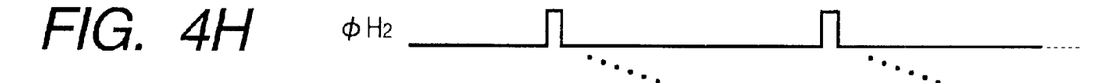
Figure 4I:
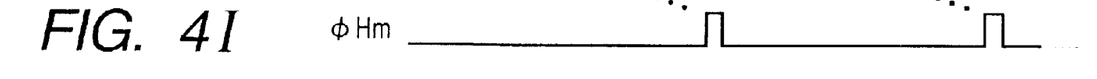
Figure 4J:
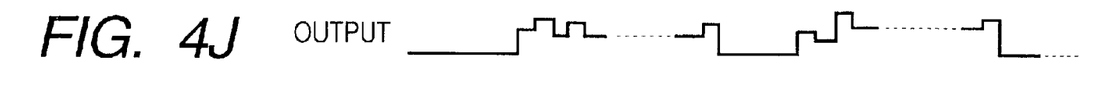

As shown in FIG. 4F, $\phi H_0$ is output from the horizontal shift register 131, and the horizontal switching MOS transistor 135 is turned on. As a consequence, as shown in FIG. 4J, signal charge is output from the vertical reading line 141 to the horizontal reading line 142. Subsequently, $\phi H_1$, $\phi H_2$, ..., $\phi H_m$ are sequentially output from the horizontal shift register 131, as shown in FIGS. 4G to 4I, and signal charges corresponding to one-line pixels in the row direction are sequentially output to the horizontal reading line 142, as shown in FIG. 4J. With the above operation, one-line reading operation in the row direction is complete.

As shown in FIG. 4C, $\phi C_n$ is output from the vertical shift register 130 to the AND gate 132, and the reset MOS transistor 136 is turned on. With this operation, the signal charge in the photoelectric conversion element 139 is initialized (reset). In addition, the signal charges in pixel portions on another line in the row direction are reset in the same manner, and charges are newly accumulated in photoelectric conversion elements during the next accumulation period.

Subsequently, as shown in FIG. 4D, $\phi O_{n+1}$ is output from the vertical shift register 130 to a pixel (not shown) on the second line, and the vertical output switching MOS transistor 137 is turned on. With this operation, the signal charge in the photoelectric conversion element 139 of the pixel portion on the second line is output to the vertical reading line 141. In addition, as shown in FIGS. 4F to 4I, $\phi H_0$ to $\phi H_m$ are sequentially output from the horizontal shift register 131, and the signal charges on the vertical reading line 141 are sequentially output to the horizontal reading line 142, as shown in FIG. 4J.

As shown in FIG. 4E, $\phi C_{n+1}$ is output from vertical shift register 130 to the AND gate 132, and the photoelectric conversion element 139 of the pixel portion on the second line is reset. Subsequently, signal charges are read from the pixel portions on the third line, fourth line, . . . . When the signal charge on the last line, i.e., the nth line, is read, reading of signal charges from all the pixel portions of the X-ray image sensing panel 120 is complete.

Figure 5A:
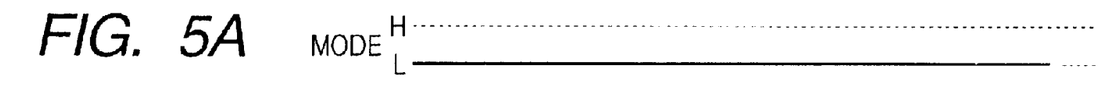
FIGS. 5A, 5B, 5C, 5D, 5E, 5F, 5G, 5H, 5I and 5J are timing charts showing non-destructive reading operation.

Non-destructive reading operation without reset will be described next with reference to FIGS. 5A to 5J. In normal reading operation, after signal charges are read from photoelectric conversion elements, the signal charges are reset, as described above. In contrast to this, in non-destructive reading operation, after signal charges are read from photoelectric conversion elements, the signal charges are not reset. In this case, therefore, as shown in FIG. 5A, a low-level mode switching signal is supplied from the mode switching circuit 121 to the X-ray image sensing panel 120, and the AND gate 132 is kept disabled.

Figure 5B:
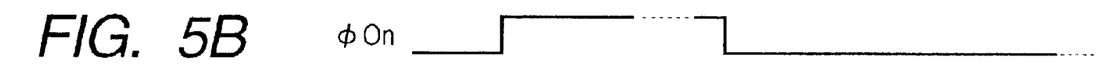
Figure 5C:
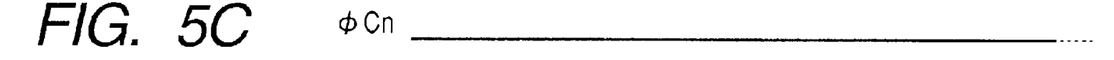

In this state, $\phi O_n$ is output from the vertical shift register 130 as shown in FIG. 5B, and the vertical output switching MOS transistor 137 is turned on. With this operation, the signal charge in the photoelectric conversion element 139 is output to the vertical reading line 141 through the reading MOS transistor 138. As shown in FIG. 5F, $\phi H_0$ is output from the horizontal shift register 131 to turn on the horizontal switching MOS transistor 135. As a consequence, as shown in FIG. 5J, the signal charge is output from the vertical reading line 141 to the horizontal reading line 142. Subsequently, as shown in FIGS. 5G to 5I, $\phi H_1$, $\phi H_2$, . . . , $\phi H_m$ are sequentially output from the horizontal shift register 131, and signal charges are output from pixel portions corresponding to one line in the row direction to the horizontal reading line 142. With the above operation, reading operation corresponding to one line in the row direction is completed.

Figure 5D:
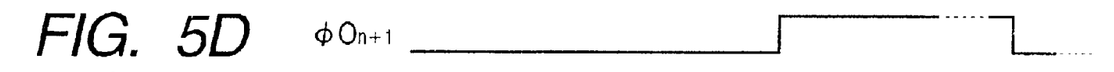
Figure 5E:
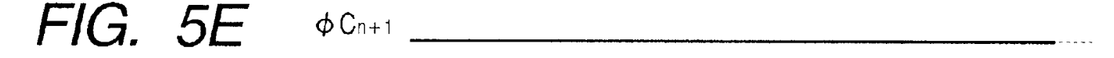
Figure 5F:
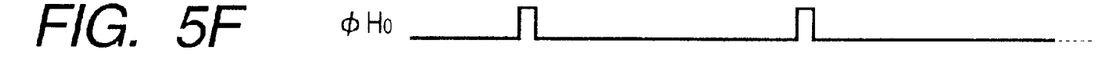
Figure 5G:
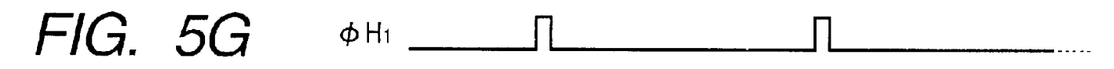
Figure 5H:
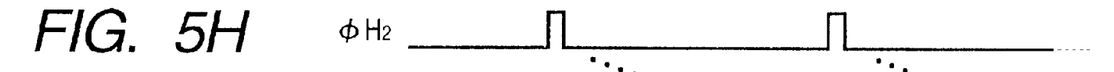
Figure 5I:
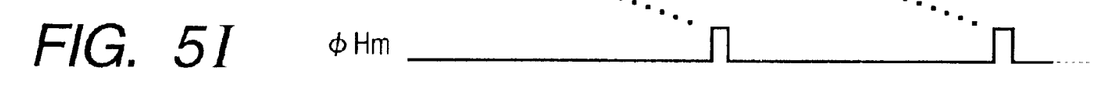
Figure 5J:
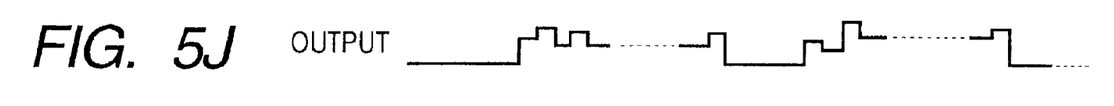

Subsequently, as shown in FIG. 5D, $\phi O_{n+1}$ is output from the vertical shift register 130 to each pixel portion (not shown) on the second line to turn on the vertical output switching MOS transistor 137. With this operation, the signal charge in the photoelectric conversion element 139 of the pixel portion on the second line is output to the vertical reading line 141. As shown in FIGS. 5F to 5I, $\phi H_0$ to $\phi H_m$ are sequentially output from the horizontal shift register 131, and the signal charges on the vertical reading line 141 are sequentially output to the horizontal reading line 142, as shown in FIG. 5J.

Subsequently, the signal charges in the pixels on the third line, fourth line, . . . , are read in the same manner. When the signal charge on the last line, i.e., the nth line, is read, reading operation of all pixel portions of the X-ray image sensing panel 120 is completed. As described above, in the non-destructive reading mode, after the signal charges in pixel portions are read, next accumulating operation starts without resetting the signal charges in the photoelectric conversion elements. That is, the charge amount of each pixel portion does not change before and after reading operation, and hence each photoelectric conversion element is not influenced by reading operation. In this embodiment, an exposure amount is controlled by using this non-destructive reading operation, and X-ray emission is stopped when the exposure amount reaches an optimal exposure amount, as will be described in detail later.

Figure 6A:
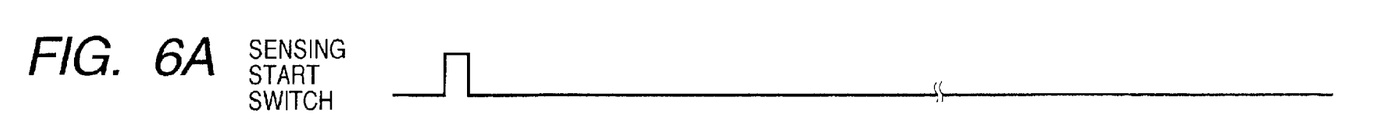
FIGS. 6A, 6B, 6C, 6D and 6E are timing charts for explaining the operation of the embodiment shown in FIG. 1.

FIGS. 6A to 6E are timing charts showing the operation of an X-ray image sensing apparatus according to this embodiment. The operation of this embodiment will be described in detail below with reference to FIGS. 1, 2, and 6A to 6E. FIG. 6A shows a sensing start signal from the sensing start switch 109. When the sensing start switch 109 is turned on, a signal for designating image sensing is supplied to the panel drive circuit 103, X-ray drive circuit 108, and mode switching circuit 121, as shown in FIG. 6A.

Figures 6B, 6C, 6D:
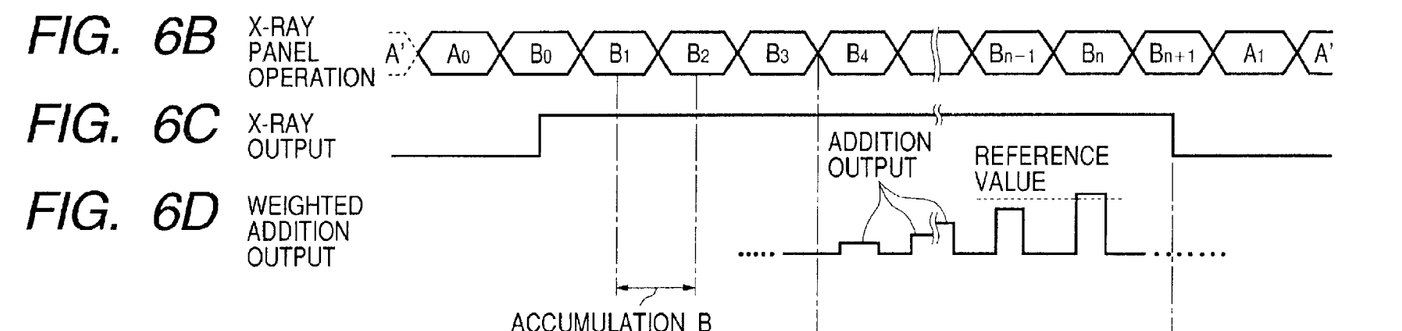

Upon reception of this start signal, the panel drive circuit 103 starts driving the X-ray image sensing panel 120. FIG. 6B shows the operation of the X-ray image sensing panel 120, which performs normal reading operation A and non-destructive reading operation B. Upon reception of the start signal, the mode switching circuit 121 supplies a mode switching signal to the X-ray image sensing panel 120. The mode switching circuit 121 supplies a high-level signal for designating normal reading operation for the first frame, i.e., the frame that is being read at this point of time, and a low-level signal for designating non-destructive reading operation for the second and subsequent frames.

As shown in FIG. 6B, the X-ray image sensing panel 120 performs normal reading operation A for the first frame, and non-destructive reading operations $B_0$, $B_1$, $B_2$, . . . for the second and subsequent frames. The X-ray drive circuit 108 drives the X-ray source 101 to emit X-rays, as shown in FIG. 6C. The X-ray source 101 starts emitting X-rays from non-destructive reading operation $B_0$ for the second frame. The X-rays pass through an object 104, and are converted into visible light by a phosphor (not shown). This light is then incident on the X-ray image sensing panel 120.

When the X-rays are emitted, the part pattern recognizing circuit 122 calculates the difference between the signal charge in non-destructive reading operation $B_2$ and the signal charge in immediately preceding non-destructive reading operation $B_1$ at the time of completion of non-destructive reading operation $B_2$. More specifically, the part pattern recognizing circuit 122 subtracts the output value from the A/D converter 110 in non-destructive reading operation $B_1$ from the output value from the A/D converter 110 in non-destructive reading operation $B_2$, and performs a calculation of OUT($B_2$)−OUT($B_1$), thereby calculating an accumulation amount B. The part pattern recognizing circuit 122 calculates accumulation amounts B for all the pixels. Although the accumulation amount B may be calculated in non-destructive reading operation $B_1$, since X-rays are unstable at the time of non-destructive reading operation $B_0$, the accumulation amount B is calculated after one frame from non-destructive reading operation $B_1$, in which X-rays are stabilized.

Figure 6E:
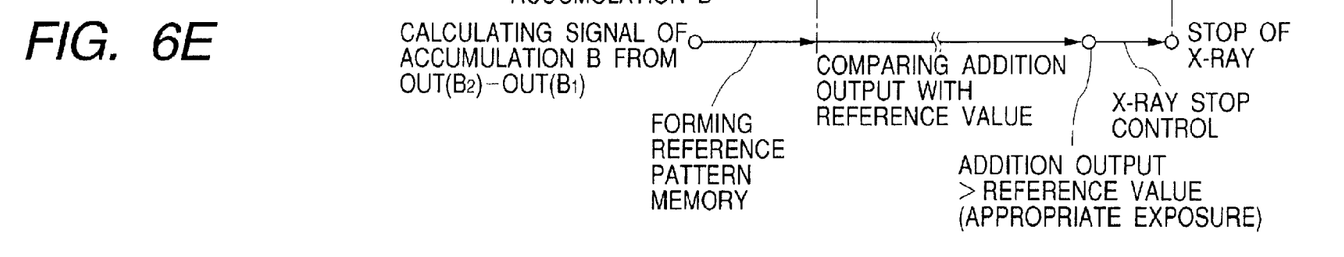

Upon calculating the accumulation amount B for each pixel, the part pattern recognizing circuit 122 performs pattern recognition on the basis of the obtained accumulation amounts B, as shown in FIG. 6E. The reference pattern optimizing circuit 123 forms the reference pattern memory 124 on the basis of the pattern recognition result, as indicated by "3" in FIG. 2. The reference value generation circuit 126 generates an REF value corresponding to the image on the basis of the pattern recognition result obtained by the part pattern recognizing circuit 122.

When the reference pattern memory 124 and REF value are generated, the multiplier 125 multiplies the numerical value of each pixel in the reference pattern memory 124 by the output value from the A/D converter 110 (i.e., the charge amount for each pixel in the X-ray image sensing panel 120) in each of frames in non-destructive reading operations $B_4$, $B_5$, . . . , and outputs the resultant values to the adder 127. The adder 127 adds the numerical values for the respective pixels, obtained by multiplication, as indicated by "4" in FIG. 2, and outputs the resultant value to the comparator 107. The multiplier 125 and adder 127 perform such processing for each of the frames in non-destructive reading operations $B_4$, $B_5$, . . . . As a result, the output value from the adder 127 gradually increases, as shown in FIG. 6D.

The comparator 107 compares the output value from the adder 127 with the REF value. When the output value from the adder 127 exceeds the REF value (Σ output>REF value), as shown in FIG. 6D, the comparator 107 outputs to the X-ray drive circuit 108 a stop signal for the X-ray source 101 to stop X-ray emission from the X-ray source 101. That is, it is determined that the current exposure amount has reached an appropriate exposure amount, as shown in FIG. 6E, and control is performed to stop X-ray emission, thus stopping X-ray emission from the X-ray source 101, as shown in FIG. 6C.

When X-ray emission is stopped, the mode switching circuit 121 outputs a low-level signal for designating normal reading operation to the X-ray image sensing panel 120. With this operation, as shown in FIG. 6B, signal charge is read from the X-ray image sensing panel 120 in normal reading operation $A_1$, and the image processing circuit 111 performs a calculation of $OUT(A_1)-OUT(A_0)$ by using the signal charge in normal reading operation $A_0$ for the first frame and the signal charge in normal reading operation $A_1$, and outputs the resultant value. Obviously, this calculation is performed for all pixels. With this operation, an output having undergone FPN correction can be obtained, and the image processing circuit 111 displays the image sensed by using the obtained output on the monitor 112. In addition, the sensed image is stored as image data in the recording medium 113. This embodiment has exemplified the case where a calculation of $OUT(A_1)-OUT(A_0)$ is performed by the image processing circuit. However, a difference circuit may be set in the X-ray image sensing panel.

To increase the reading speed in non-destructive reading operation, signal charge may be read from the X-ray image sensing panel 120 for each pixel by a thinning-out reading operation, a pixel addition reading operation, or a random access reading operation of reading only at valid reference positions (positions where numerical values in the reference pattern memory are not 0). Even if random access reading operation is performed, in particular, since no change in charge occurs before and after reading operation, there is no influence on subsequent frames. This is a characteristic feature of non-destructive reading.

Figure 7:
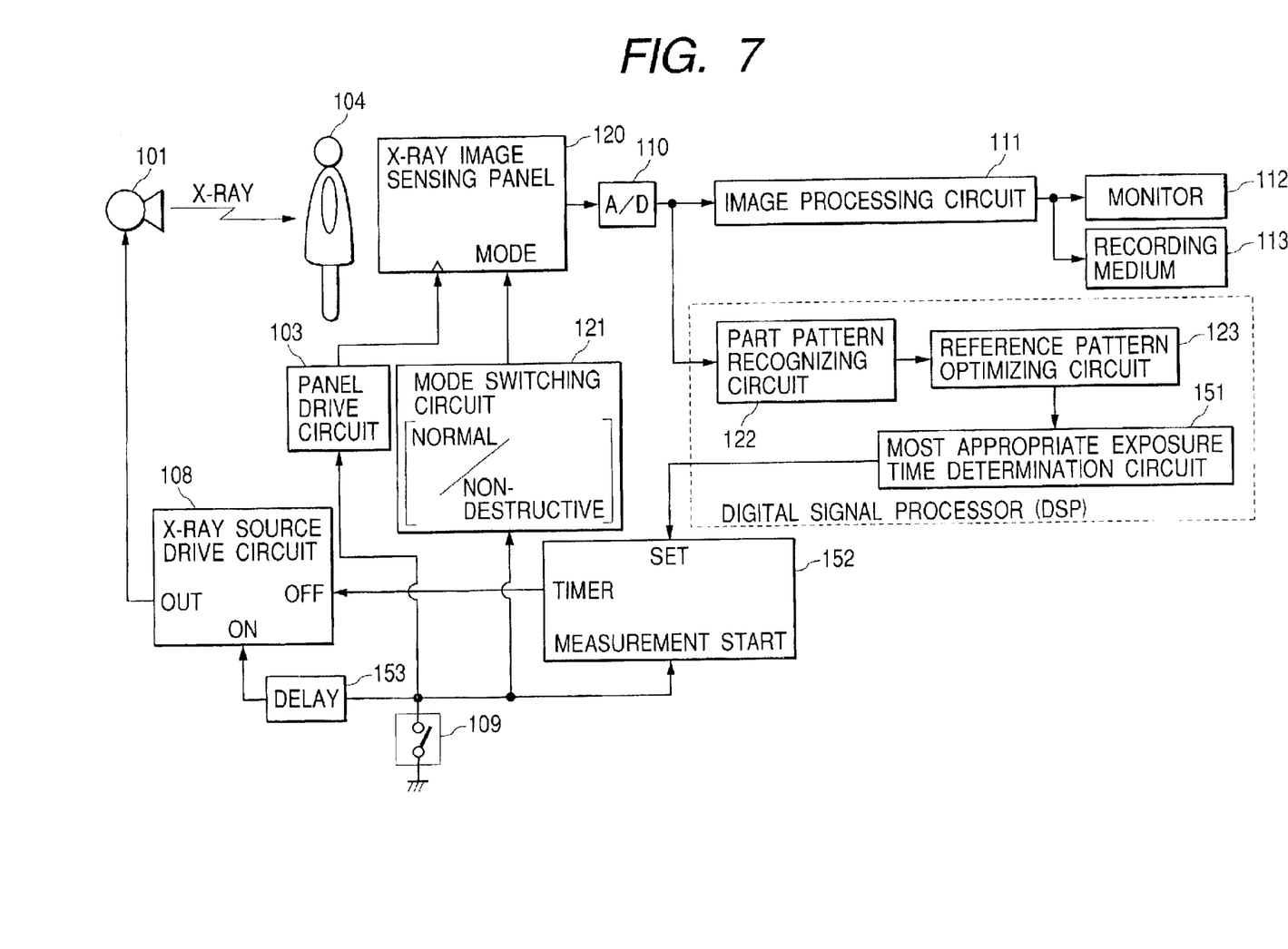
FIG. 7 is a block diagram showing the arrangement of the second embodiment of the present invention.

The second embodiment of the present invention will be described next. FIG. 7 is a block diagram showing the arrangement of an X-ray image sensing apparatus according to the second embodiment of the present invention. The same reference numerals as in FIG. 1 denote the same parts in FIG. 7, and a description thereof will be omitted. In this embodiment, a most appropriate exposure time determination circuit 151 determines a most appropriate exposure time, and the obtained most appropriate exposure time is set as a timer end value in a timer 152. A delay 153 is a delay circuit for delaying the start of driving of an X-ray drive circuit 108 by a predetermined period of time when a sensing start switch 109 is turned on.

Although not shown in FIG. 7, a reference pattern optimizing circuit 123 incorporates a reference pattern memory 124, multiplier 125, reference value generation circuit 126, and adder 127 in FIG. 1. The reference pattern optimizing circuit 123 therefore calculates a weighted addition value on the basis of the recognition result obtained by a part pattern recognizing circuit 122 in the above-described manner, and outputs it to the most appropriate exposure time determination circuit 151. The method of calculating a weighted addition value used in this embodiment is the same as that in the first embodiment. When a weighted addition value is output, the most appropriate exposure time determination circuit 151 determines a most appropriate exposure time on the basis of that output value.

More specifically, letting a be a weighted addition value and REF be the REF value generated by the reference value generation circuit 126, the most appropriate exposure time determination circuit 151 calculates $(REF/\alpha)=t$, and determines the obtained time t as a most appropriate exposure time. The obtained most appropriate exposure time t is set as a timer end value in the timer 152. When the timer 152 set to the end value t in exposure operation, a stop signal is output to the X-ray drive circuit 108 to stop X-ray emission. Note that the part pattern recognizing circuit 122, reference pattern optimizing circuit 123, and most appropriate exposure time determination circuit 151 are formed by DSPs (Digital Signal Processors).

In this embodiment, the control circuit for performing control to stop emission of radiation from the radiation source on the basis of the signal obtained by non-destructive reading from the X-ray image sensing panel is constituted by the part pattern recognizing circuit, reference pattern optimizing circuit, most appropriate exposure time determination circuit, and timer. However, this circuit may be constituted by only the most appropriate exposure time determination circuit and timer and designed to compare the signal obtained by non-destructive reading with a predetermined reference value, obtain a most appropriate exposure time in accordance with the comparison result, and stop X-ray emission.

Figure 8A:
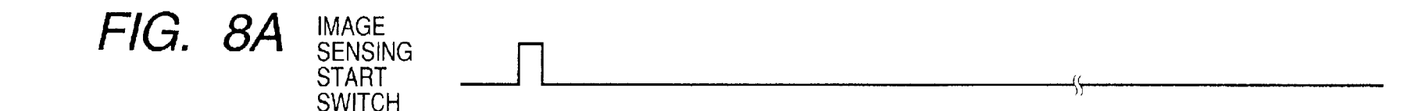
FIGS. 8A, 8B, 8C, 8D and 8E are timing charts for explaining the operation of the embodiment shown in FIG. 7.
Figure 8B:
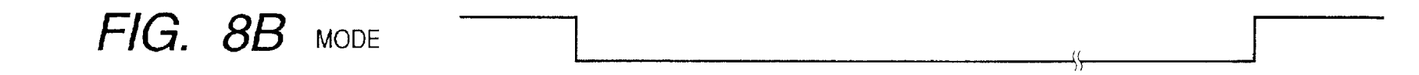
Figure 8C:
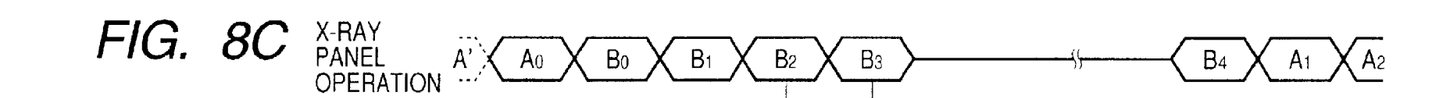

FIGS. 8A to 8E are timing charts showing the operation of the second embodiment. The operation of this embodiment will be described below with reference to FIGS. 7, 8A to 8E. When the sensing start switch 109 is turned on, a signal for designating the start of image sensing operation is supplied to a panel drive circuit 103, a mode switching circuit 121, the timer 152, and the delay 153, as shown in FIG. 8A. Upon reception of the start signal, the panel drive circuit 103 starts driving an X-ray image sensing panel 120, as shown in FIG. 8C, and a signal is read from the X-ray image sensing panel 120.

Figure 8D:
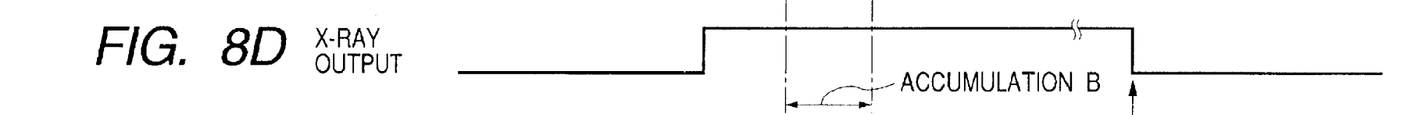
Figure 8E:
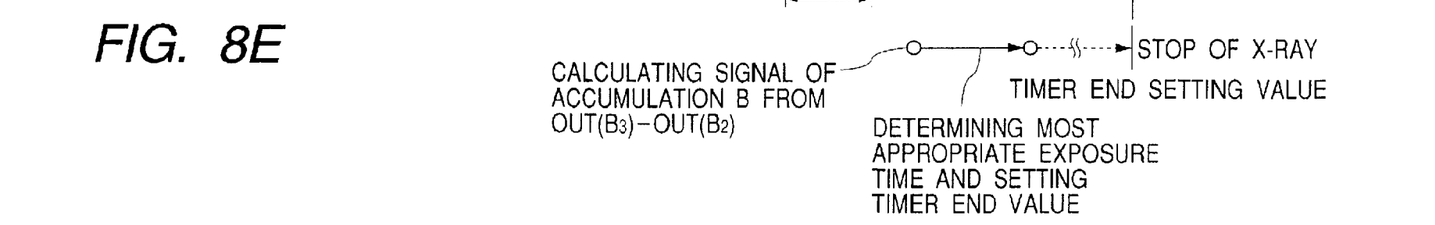

At this time, as shown in FIG. 8B, a mode switching signal from the mode switching circuit 121 is at high level, and the first frame, i.e., the frame that is being read at this time, is read by normal reading operation A. Thereafter, as shown in FIG. 8B, the mode switching signal is switched to low level to switch the reading mode to the non-destructive reading mode. The start of driving of the X-ray drive circuit 108 is delayed from the timing of the start signal by the delay 153, and the X-ray source 101 starts emitting X-rays after non-destructive reading operation $B_0$ for the second frame is completed, as shown in FIG. 8D. This operation is provided to obtain the signal by non-destructive reading operation before the start of X-ray emission, as will be described later.

After the reading mode is switched to the non-destructive reading mode, signal charges are read from the X-ray image sensing panel 120 by non-destructive reading operations $B_0$, $B_1$, $B_2$, ..., as shown in FIG. 8C. When non-destructive reading operation $B_3$ is complete, the part pattern recognizing circuit 122 calculates an accumulation amount B by using the charge amount of the frame in non-destructive reading operation $B_3$ and the charge amount of the immediately preceding frame in non-destructive reading operation $B_2$. That is, the part pattern recognizing circuit 122 calculates the accumulation amount B by performing a calculation of $OUT(B_3)-OUT(B_2)$. After the completion of non-destructive reading operation $B_3$, the reading operation is interrupted, as shown in FIG. 8C. The accumulation amount B is used for pattern recognition, the formation of a reference pattern memory and REF value, the calculation of a weighted addition value, and the like as in the first embodiment.

The most appropriate exposure time determination circuit 151 determines a most appropriate exposure time by using a weighted addition value, and sets the obtained most appropriate exposure time t as a timer end value in the timer 152, as described above. When the timer 152 times the set time, the timer 152 outputs to the X-ray drive circuit 108 a signal to instruct an X-ray source 101 to stop driving, thereby stopping X-ray emission from the X-ray source 101, as shown in FIG. 8D. When X-ray emission is stopped, non-destructive reading operation B4 is performed, as shown in FIG. 8C. Thereafter, the mode switching signal is switched to high level to perform normal reading operations $A_0$, $A_1$, ..., as shown in FIG. 8B.

When non-destructive reading operation $B_4$ is complete, an image processing circuit 111 calculates $OUT(B_4)-OUT(B_0)$ by using the charge amounts obtained by non-destructive reading operations $B_0$ and $B_4$, and outputs the resultant value. This calculation is performed for all pixels. The image processing circuit 111 displays the image sensed by using the obtained output on a monitor 112 or stores it as image data in a recording medium 113. As the X-ray image sensing panel 120, a panel having pixel portions arranged two-dimensionally is used. However, a panel having pixel portions arranged one-dimensionally may be used. In this embodiment, the image processing circuit calculates $OUT(A_1)-OUT(B_0)$. However, the X-ray image sensing panel may incorporate a difference circuit.

In the first embodiment, since $OUT(B_0)-OUT(A_0)=$ output, $OUT(B_0)$ and $OUT(A_0)$ contain different KTC noise components. Even if, therefore, $OUT(B_0)$ is subtracted from $OUT(A_0)$, $KTC(A_0)$ contained in $OUT(A_0)$ does not cancel out $KTC(B_0)$ contained in $OUT(B_0)$. Since KTC noise is random noise, $\sqrt{2} \times KTC$ noise remains.

In the second embodiment, $OUT(B_0)$ and $OUT(A_1)$ of output=$OUT(A_1)-OUT(B_0)$ contain the same amount of KTC noise produced by normal reading operation $A_0$. If, therefore, $OUT(B_0)$ is subtracted from $OUT(A_1)$, the KTC noise contained in $OUT(B_0)$ cancel out the KTC noise contained in $OUT(A_1)$. Hence, an output free from the influence of KTC noise can be obtained. This is because no normal reading operation is performed between non-destructive reading operations $B_0$ and $A_1$.

In addition, even if output=$OUT(A_1)-OUT(B_0)$ is calculated by using $OUT(B_0)$ obtained by normal reading operation instead of the output obtained by non-destructive reading operation $B_4$, an output free from the influence of KTC noise can be obtained. This is because $OUT(B_0)$ also contains the KTC noise produced by normal reading operation $A_0$. That is, an excellent radiation image sensing output containing no KTC noise can be obtained by subtracting the non-destructive reading output obtained by the image sensing means before radiation emission from the output obtained by the images sensing means obtained after radiation emission.

In the first embodiment, since whether X-ray emission is to be stopped is determined while non-destructive reading operation B is performed, the X-ray stop timing coincides with the cycle of non-destructive reading operation B, and X-ray emission cannot be stopped during non-destructive reading operation B. In contrast to this, according to the second embodiment, since X-ray emission can be stopped in accordance with the time obtained by the most appropriate exposure time determination circuit 151, the X-ray stop timing can be controlled more finely than in the first embodiment.

In each embodiment described above, a phosphor is used to convert X-rays into visible light. However, a general scintillator, i.e., a wavelength converter, may be used. In addition, this apparatus may use photoelectric elements that directly detect radiation and generate charge instead of using a phosphor.

Although each embodiment has exemplified the case where X-rays are used, radiation such as α, β, or γ ray may be used.

As has been described above, according to the first and second embodiments, optimal image sensing can be performed without requiring any cumbersome operation, and a high-quality image without a decrease in S/N ratio can be obtained. In addition, since no phototimer unit is used, image sensing can be accurately performed regardless of deviations from appropriate image sensing positions and the like. This makes it possible to reduce a deterioration in a S/N ratio and manufacture an apparatus at a low cost.

Many widely different embodiments of the present invention may be constructed without departing from the spirit and scope of the present invention. It should be understood that the present invention is not limited to the specific embodiments described in the specification, except as defined in the appended claims.

What is claimed is:

1. A radiation image sensing apparatus comprising:
   an image sensing unit which is capable of nondestructively reading and includes a plurality of pixel portions for sensing an object image by passing radiation from a radiation source through an object;
   a drive circuit which drives said image sensing unit so that a first signal which is obtained by resetting said plurality of pixel portions is read out nondestructively from said image sensing unit, thereafter a signal is read out nondestructively a plurality of times from said image sensing unit without resetting, and subsequently a second signal is read out nondestructively from said image sensing unit without resetting said plurality of pixel portions;
   a differential circuit which effects differential operation of the first signal and the second signal; and
   a control circuit which effects control to stop emission of radiation from the radiation source on the basis of a signal non-destructively read out from said image sensing unit by said drive circuit.

2. An apparatus according to claim 1, further comprising a switching circuit which switches reading modes of said image sensing unit, said switching circuit switching the reading mode of said image sensing unit to a non-destructive reading mode in the image sensing operation.

3. An apparatus according to claim 1, wherein the pixel portion includes a photoelectric conversion element and a reading transistor, the photoelectric conversion element of the pixel portion being connected to a control terminal of the reading transistor.

4. An apparatus according to claim 3, wherein a load is connected to one main electrode terminal of the reading transistor, and the transistor is formed by an amplifier having a voltage amplification factor of substantially 1.

5. An apparatus according to claim 4, wherein the load is a constant current source or a resistor.

6. An apparatus according to claim 3, wherein a switching transistor which selects a pixel portion in a row direction is connected in series with the reading transistor.

7. An apparatus according to claim 3, wherein a reset transistor is connected in series with the photoelectric conversion element, and the reset transistor is controlled in accordance with a mode switching signal to switch the reading mode to a normal reading mode or a non-destructive reading mode.

8. An apparatus according to claim 1, wherein said control circuit comprises a pattern recognizing circuit which performs pattern recognition on the basis of an output from said image sensing unit, a detection circuit which detects a radiation amount on the basis of the pattern recognition result obtained by the pattern recognizing circuit, and a generation circuit which generates a reference value for a most appropriate radiation amount on the basis of the pattern recognition result obtained by the pattern recognizing circuit.

9. An apparatus according to claim 8, wherein said reference value is generated for a most appropriate radiation amount on the basis of the pattern recognition result obtained by the pattern recognizing circuit.

10. An apparatus according to claim 8, wherein said control circuit detects a radiation amount by using the detection circuit while performing non-destructive reading from said image sensing unit in the image sensing operation, and stops emission of radiation from the radiation source when the radiation amount becomes not less than the reference value.

11. An apparatus according to claim 8, wherein said control circuit detects a most appropriate image sensing time while performing non-destructive reading from said image sensing unit in the image sensing operation, and stops emission of radiation from the radiation source when the image sensing time reaches the most appropriate image sensing time.

12. An apparatus according to claim 8, wherein said control circuit includes an addition circuit which adds outputs from said image sensing unit.

13. An apparatus according to claim 12, wherein the addition circuit performs weighted addition based on a reference pattern.

14. An apparatus according to claim 13, wherein the reference pattern is generated on the basis of the pattern recognition result.

15. An apparatus according to claim 1, further comprising a difference circuit which obtains a radiation image sensing output by subtracting an output from said image sensing unit which is obtained before emission of radiation from an output from said image sensing unit which is obtained after emission of radiation from the radiation source is stopped.

16. An apparatus according to claim 1, wherein the first signal is read out after said plurality of pixel portions are reset in a time period from a time when a sensing start switch for driving the radiation source is turned on to a time when the emission of the radiation starts.

17. An image sensing method for a radiation image sensing apparatus including an image sensing unit which senses an object image by converting the object image on the basis of radiation from a radiation source passing through an object into an electric signal, comprising the step of stopping emission of radiation from the radiation source on the basis of a signal obtained by non-destructively reading the electric signal from the image sensing unit during sensing of the object image by the image sensing unit.

18. A radiation image sensing apparatus comprising:
an image sensing unit which is capable of nondestructively reading and includes a plurality of pixel portions for sensing an object image by passing radiation from a radiation source through an object;
a drive circuit which drives said image sensing unit so that a first signal which is obtained by resetting said plurality of pixel portions is read out nondestructively from said image sensing unit, thereafter a signal is read out nondestructively a plurality of times from said image sensing unit without resetting, and subsequently a second signal is read out nondestructively from said image sensing unit without resetting said plurality of pixel portions;
a differential circuit which effects differential operation of the first signal and the second signal;
a control circuit which stops emission of the radiation from the radiation source by comparing with a reference level a signal level of a signal which is obtained by reading out an electric signal nondestructively from said image sensing unit during sensing of the object image by said image sensing unit, wherein said control circuit changes the reference level in accordance with the object.

19. An apparatus according to claim 18, wherein said control circuit detects object information from the signal obtained by reading out the electric signal nondestructively from said image sensing unit, and changes the reference level on the bases of the detected object information in accordance with the object.

20. An apparatus according to claim 18, wherein the signal obtained by reading out the electric signal nondestructively from said image sensing unit is also a signal which is read out from said image sensing unit through thinning-out read-out.

21. An apparatus according to claim 18, wherein the signal obtained by reading out the electric signal nondestructively from said image sensing unit is also a signal which is read out from said image sensing unit through addition thereof.

* * * * *

UNITED STATES PATENT AND TRADEMARK OFFICE
CERTIFICATE OF CORRECTION

PATENT NO. : 6,847,698 B2
DATED : January 25, 2005
INVENTOR(S) : Noriyuki Kaifu et al.

It is certified that error appears in the above-identified patent and that said Letters Patent is hereby corrected as shown below:

Column 4,
Line 55, "much" should read -- many --.

Column 6,
Line 24, "Such the small" should read -- Such small --.

Column 10,
Line 24, "letting a" should read -- letting α --.
Line 30, "152 set" should read -- 152 is set --.

Column 11,
Line 34, "operation B4" should read -- operation $B_4$ --.
Line 63, "cancel" should read -- cancels --.

Column 12,
Line 11, "images" should read -- image --.

Signed and Sealed this

Seventh Day of February, 2006

JON W. DUDAS
*Director of the United States Patent and Trademark Office*